US008071098B2

(12) United States Patent
Nishibori et al.

(10) Patent No.: US 8,071,098 B2
(45) Date of Patent: Dec. 6, 2011

(54) METHOD OF PREVENTING CEREBRAL VASOSPASM WITH ANTI-HMGB1 ANTIBODY

(75) Inventors: Masahiro Nishibori, Okayama (JP); Shuji Mori, Okayama (JP); Hideo Takahashi, Okayama (JP); Yasuko Tomono, Okayama (JP); Isao Date, Okayama (JP); Shigeki Ono, Okayama (JP)

(73) Assignee: National University Corporation Okayama University, Okayama (JP)

( * ) Notice: Subject to any disclaimer, the term of this patent is extended or adjusted under 35 U.S.C. 154(b) by 0 days.

(21) Appl. No.: 12/227,292

(22) PCT Filed: May 18, 2007

(86) PCT No.: PCT/JP2007/060231
§ 371 (c)(1),
(2), (4) Date: Nov. 13, 2008

(87) PCT Pub. No.: WO2007/135992
PCT Pub. Date: Nov. 29, 2007

(65) Prior Publication Data
US 2009/0175878 A1    Jul. 9, 2009

(30) Foreign Application Priority Data
May 19, 2006 (JP) .................................. 2006-140773

(51) Int. Cl.
*A61K 39/395* (2006.01)
(52) U.S. Cl. .................................. 424/145.1; 424/158.1
(58) Field of Classification Search ............................ None
See application file for complete search history.

(56) References Cited

U.S. PATENT DOCUMENTS

| | | | |
|---|---|---|---|
| 5,770,772 A | 6/1998 | Aono et al. | |
| 6,004,986 A * | 12/1999 | Arthur et al. | 514/348 |
| 6,303,321 B1 | 10/2001 | Tracey et al. | |
| 6,468,533 B1 | 10/2002 | Tracey et al. | |
| 6,610,713 B2 | 8/2003 | Tracey et al. | |
| 6,646,006 B2 * | 11/2003 | Cooke et al. | 514/565 |
| 6,838,471 B2 | 1/2005 | Tracey et al. | |
| 7,060,504 B2 | 6/2006 | Tracey et al. | |
| 7,097,838 B2 | 8/2006 | Tracey et al. | |
| 7,125,567 B2 * | 10/2006 | Sugi et al. | 424/497 |
| 7,220,723 B2 | 5/2007 | Tracey et al. | |
| 7,288,250 B2 * | 10/2007 | Newman et al. | 424/133.1 |
| 7,304,034 B2 | 12/2007 | Tracey et al. | |
| 2002/0102609 A1 | 8/2002 | Tracey et al. | |
| 2003/0017155 A1 | 1/2003 | Tracey et al. | |
| 2003/0060410 A1 | 3/2003 | Tracey et al. | |
| 2003/0113323 A1 | 6/2003 | Tracey et al. | |
| 2004/0005316 A1 | 1/2004 | Tracey et al. | |
| 2006/0035851 A1 | 2/2006 | Bianchi et al. | |
| 2006/0210565 A1 | 9/2006 | Tracey et al. | |
| 2006/0240019 A1 | 10/2006 | Tracey et al. | |
| 2008/0305073 A1 * | 12/2008 | Barone et al. | 424/85.2 |

FOREIGN PATENT DOCUMENTS

| | | |
|---|---|---|
| JP | 2002-60346 | 2/2002 |
| JP | 2003-520763 | 7/2003 |
| JP | 2004-510695 | 8/2004 |
| JP | 2005-120070 | 5/2005 |
| JP | 2005-512507 | 5/2005 |
| JP | 2005-537253 | 12/2005 |
| JP | 3882090 | 2/2007 |
| WO | 00/47104 | 8/2000 |
| WO | 02/092004 | 11/2002 |
| WO | 2004/004763 | 1/2004 |
| WO | 2006/124477 | 11/2006 |

OTHER PUBLICATIONS

Tachikawa et al., J. Nihon Univ. Med. Ass. 62: 469-479, 2002.*
International Search Report issued Jun. 12, 2007 in the International (PCT) Application No. PCT/JP2007/060231 of which the present application is the U.S. National Stage.
European Search Report issued Apr. 23, 2009 in the European patent Application No. 07743666.5 which is a counterpart of the present application.
Isao Date, et al., "Gene therapy against cerebral vasospasm after subarachnoid hemorrhage", Brain and Circulation; Medical View Co., Ltd., published in 2002, vol. 7, No. 1, pp. 47-51 ISSN 1341-8440, with a Brief explanation of the document in English.
Ikuro Maruyama, "Surgical trauma in living body and HMGB1: delayed biological lethal factor", Surgical Trauma and Immunity; Medical Review Co., Ltd., published in 2006, pp. 31-36 with a Brief explanation of the document in English.
George Bowman, et al. "A Novel Inhibitor of Inflammatory Cytokine Production (CNI-1493) Reduces Rodent Post-Hemorrhagic Vasospasm" Neurocritical Care, Humana Press, Totowa, NJ, US, vol. 5, No. 3, published Jan. 1, 2006, pp. 222-229.
Sajjad Muhammad, et al. "The HMGB1 Receptor RAGE Mediates Ischemic Brain Damage" Journal of Neuroscience, New York, NY, US, vol. 28, No. 46, published Nov. 1, 2008, pp. 12023-12031.
Extended European Search Report issued Dec. 7, 2009 in related European Application No. 06811724.1.
K. Liu et al., "Anti-high mobility group box 1 monoclonal antibody ameliorates brain infarction induced by transient ischemia in rats", The FASEB Journal, vol. 21, No. 14, pp. 3904-3916, Dec. 2007.

(Continued)

Primary Examiner — Phillip Gambel
(74) Attorney, Agent, or Firm — Wenderoth, Lind & Ponack, L.L.P.

(57) ABSTRACT

An objective of the present invention is to provide a cerebral vasospasm inhibitor which is effective on cerebral vasospasm occurring after subarachnoid hemorrhage and has few side-effects. The cerebral vasospasm inhibitor of the invention is characterized in containing an anti-HMGB1 monoclonal antibody as an active ingredient.

5 Claims, 4 Drawing Sheets

OTHER PUBLICATIONS

Reply to the ISR (plus English translation) filed in related application No. PCT/JP2006/320436.

English translation of "Certified Experiment Results", as referenced on p. 9 of the "Reply to the ISR" (see above).

E. Abraham et al., "Cutting Edge: HMG-1 as a Mediator of Acute Lung Inflammation", The Journal of Immunology, The American Association of Immunologists (2000), vol. 65, pp. 2950-2954.

H. Yang et al., "The Cytokine Activity of HMGB1", Journal of Leukocyte Biology, Jul. 2005, vol. 78, No. 1, pp. 1-8.

K.A. O'Connor et al., "Further characterization of high mobility group box 1 (HMGB1) as a proinflammatory cytokine: central nervous system effects", Cytokine (2003), vol. 24, pp. 254-265.

N. Vila et al., "Proinflammatory cytokines and early neurological worsening in ischemic stroke", Stroke (2000), vol. 31, No. 10, pp. 2325-2329.

SL. Liao et al., "Association of Immune Responses and Ischemic Brain Infarction in Rat", Neuroreport (2001), vol. 12, No. 9, pp. 1943-1947.

Office Action dated Sep. 3, 2009 in U.S. Appl. No. 12/084,044, the national stage application to related application No. PCT/JP2006/320436.

International Search Report and PCT/IB/338 in related application No. PCT/JP2006/320436.

International Search Report and PCT/IB/338 of corresponding application No. PCT/JP2007/060231.

Reply to the ISR (plus English translation) filed in the corresponding application No. PCT/JP2007/060231.

English translation of "Certified Experiment Results".

"Explanation of Circumstances Concerning Accelerated Examination" (English translation) filed in related application No. JP 2005-308949.

"Notice of Reasons for Refusal" dated May 30, 2006 issued in related application No. JP 2005-308949.

A. Williams et al., "Delayed Treatment of Ischemia/Reperfusion Brain Injury", Stroke (2004), vol. 35, No. 5, pp. 1186-1191.

R. Berti et al., "Quantitative real-time RT-PCR analysis of inflammatory gene expression associated with ischemia-reperfusion brain injury", Journal of Cerebral Blood Flow and Metabolism (2002), vol. 22, No. 9, pp. 1068-1079.

Koroshetz, Walter J. and Michael A. Moskowitz, "Emerging treatments for stroke in humans", Journal of Cerebral Blood Flow and Metabolism, Sep. 2002, vol. 22, No. 9, pp. 227-233.

European Office Action issued Oct. 6, 2010 in European Application 06811724.1 corresponding to CIP U.S. Appl. No. 12/654,790.

Y. Yamasaki et al., "Interleukin-1 as a Pathogenetic Mediator of Ischemic Brain Damage in Rats," Stroke, vol. 26, No. 4, pp. 676-681, 2005.

F.C. Barone et al., "Tumor Necrosis Factor-$\alpha$: A Mediator of Focal Ischemic Brain Injury," Stroke, vol. 28, No. 6, pp. 1233-1244, 1997.

A. Mizuno et al., "Inhibitory Effect of MCI-186, a Free Radical Scavenger, on Cerebral Ischemia Following Rat Middle Cerebral Artery Occlusion," General Pharmacology, vol. 30, No. 4, pp. 575-578, 1998.

M.E. Sughrue et al., "Review: Anti-adhesion molecule strategies as potential neuroprotective agents in cerebral ischemia: A critical review of the literature," Inflammation Research, vol. 53, pp. 497-508, 2004.

Chinese Office Action dated Feb. 1, 2011 issued in corresponding Chinese Patent Application No. 200780018253.X.

Office Action dated Mar. 22, 2011 issued in the related U.S. Appl. No. 12/654,790.

European Office Action issued Aug. 11, 2011 in related European Application No. 06 811 724.1.

* cited by examiner

Before   After

```
SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Glu Glu Glu Asp Asp Asp Asp Glu
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Asp Asp Asp Asp Glu
1               5
```

METHOD OF PREVENTING CEREBRAL VASOSPASM WITH ANTI-HMGB1 ANTIBODY

This application is a U.S. national stage of International Application No. PCT/JP2007/060231 filed May 18, 2007.

TECHNICAL FIELD

The present invention relates to a medicament for inhibiting cerebral vasospasm occurring after subarachnoid hemorrhage.

BACKGROUND ART

Subarachnoid hemorrhage occurs generally in fourty- to sixtysomething virile aged persons, and refers to the condition that there is hemorrhage in the space between the brain-circumscribing arachnoid and the brain mainly as a result of aneurysm rupture. The intracranial pressure is instantaneously elevated by such a hemorrhage, to give damage to the brain. About 10% of the patients suffering from a subarachnoid hemorrhage will die immediately after the onset and about 25% will become serious, according to the statistics. Even if a patient suffering from a subarachnoid hemorrhage for the first time stays alive, re-hemorrhage is said to occur within 2 weeks in about 25% of the patient. The treatments of the subarachnoid hemorrhage include removal of hematoma and prevention of re-rupture of the ruptured aneurysm.

Subarachnoid hemorrhage itself is thus a very dreadful disease. Further, even after the treatment for subarachnoid hemorrhage, more than half of the patients may suffer from a peculiar pathological state, which is called cerebral vasospasm. Cerebral vasospasm is a reversible constriction of the cerebral main artery, which occurs in 3 to 14 days after subarachnoid hemorrhage and persists for 1 to 2 weeks. Cerebral ischemia as a result of the condition causes death in about 40% of the patients and serious sequelae in about 30%, and only about 30% can return to normal life. Accordingly, cerebral vasospasm is causing a serious problem.

In such a circumstance, however, researches concerning cerebral vasospasm have not been sufficiently promoted and neither prevention nor treatment of the disease has been established. For example, the mechanism of the development of subarachnoid hemorrhage to cerebral vasospasm remains unknown, though multiple factors including free radicals, lipid peroxidation, an arachidonate cascade, damages in the perivascular nerve, damages in endothelium-dependent relaxation, and structural change of the vascular wall have been suggested to be involved in a complicated manner. Therefore, prevention or treatment of cerebral vasospasm would be difficult if only one of these factors could be inhibited.

Fasudil hydrochloride or sodium ozagrel is currently administered as the systemic chemotherapy for cerebral vasospasm. The cisternal administration of a tissue plasminogen activator during operation for subarachnoid hemorrhage is also employed. The effect of these therapies, however, has been insufficient.

HMGB1 is a protein present in rodents to human beings, and 95% or more of the amino acid sequence thereof is common. HMGB1 exists in normal cells, and the blood level is increased by stimulation with an LPS: lipopolysaccharide which is a bacterial endotoxin released in sepsis: systemic inflammatory response syndrome, to produce tissue damage eventually. Accordingly, the method described in JP 2003-520763 T employs administration of an HMGB1 antagonist for the treatment of the symptoms by an activated inflammatory cytokine cascade. However, there is neither description nor suggestion concerning cerebral vasospasm in JP 2003-520763 T, although there is a description of many diseases and symptoms mediated by the inflammatory cytokine cascade as examples of the target diseases to be treated.

In addition, JP 2005-537253 T discloses a composition containing an HMGB1 antibody or the like for the treatment of side-effects induced by a necrotic tissue. The side effects are exemplified only by activation of viable cells in the vicinity, mobilization and activation of myelocytes, loss of barrier function of the endothelium, and edema; and there is no description or suggestion concerning cerebral vasospasm.

DISCLOSURE OF THE INVENTION

As mentioned above, there has been no established means for inhibiting cerebral vasospasm, in spite of the fact that cerebral vasospasm occurring after subarachnoid hemorrhage may be fatal or cause serious sequelae.

Accordingly, an objective to be solved by the present invention is to provide a cerebral vasospasm inhibitor which is effective on cerebral vasospasm occurring after subarachnoid hemorrhage and has few side-effects.

The inventors enthusiastically investigated various agents that were expected to be effective in inhibition of cerebral vasospasm to solve the above objective. As a result, the inventors found that an anti-HMGB1 monoclonal antibody has an effect superior to that of any agent which had been reported by then, and completed the present invention.

The cerebral vasospasm inhibitor of the present invention is characterized in comprising an anti-HMGB1 monoclonal antibody as an active ingredient.

The present invention uses an anti-HMGB1 monoclonal antibody for production of a medicament to inhibit cerebral vasospasm.

The method for inhibiting cerebral vasospasm of the present invention is characterized by administration of an anti-HMGB1 monoclonal antibody.

BEST MODE FOR CARRYING OUT THE INVENTION

Figure 1:
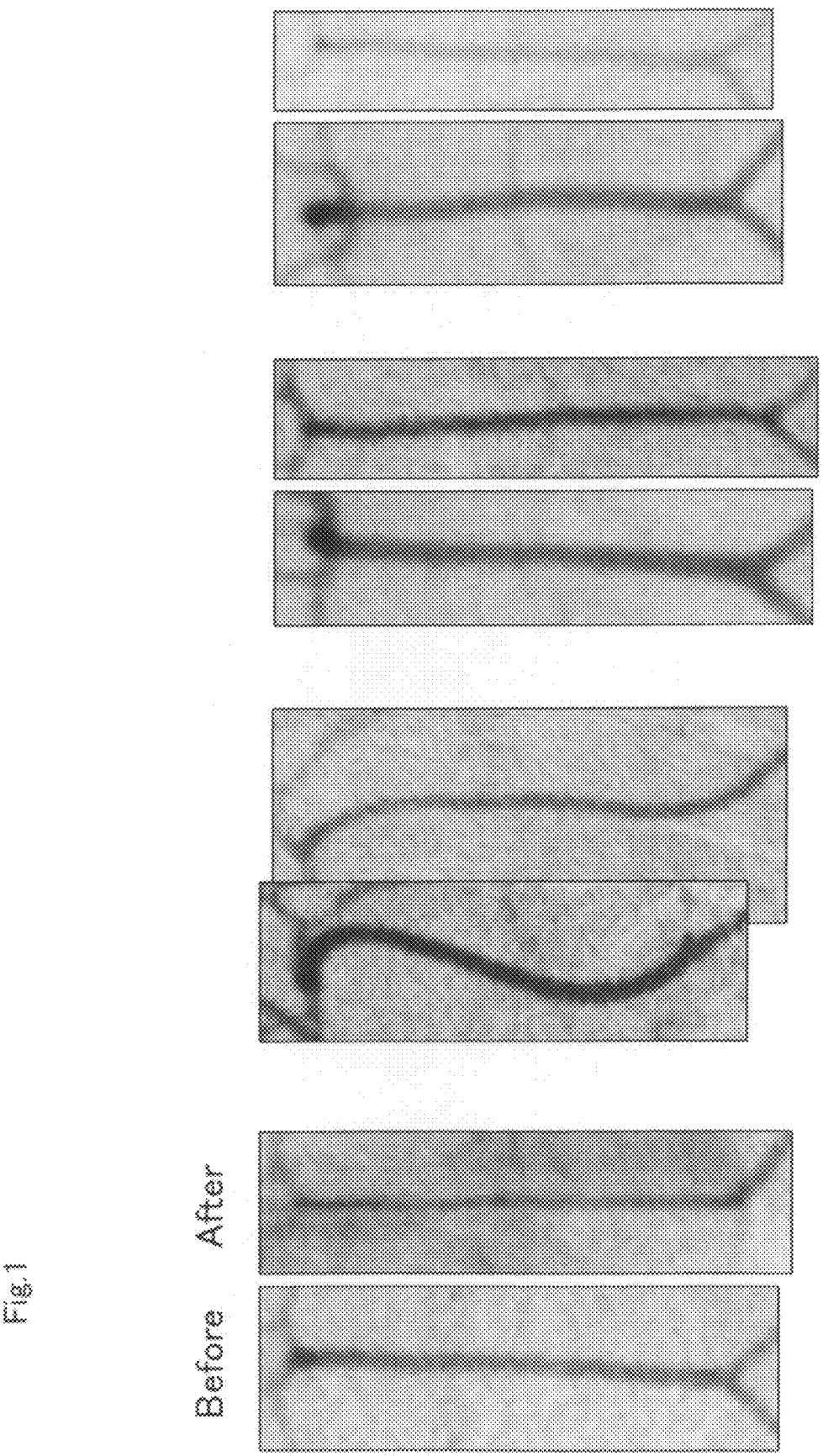
FIG. 1 is contrast images of a basilar artery before and after subarachnoid hemorrhage in an untreated animal group of subarachnoid hemorrhage model rabbits. In each pair of the photographs in the figure, a photograph before subarachnoid hemorrhage, represented as "before", is on the left; and a photograph after subarachnoid hemorrhage, represented as "after", is on the right. In each pair, the vascular diameter obviously becomes smaller, in other words, severe cerebral vasospasm is observed, after subarachnoid hemorrhage (in the right photographs).

The cerebral vasospasm inhibitor of the present invention contains an anti-HMGB1 monoclonal antibody as an active ingredient. The anti-HMGB1 monoclonal antibody acts only on HMGB1 which is one of tissue-damaging factors, and inhibits cerebral vasospasm occurring after subarachnoid hemorrhage though the action mechanism is unknown. On the other hand, the anti-HMGB1 monoclonal antibody basically does not act on any other compounds. Therefore, it is impossible or very unlikely that side-effects occur.

An anti-HMGB1 monoclonal antibody may be prepared according to a conventional method. For example, a mouse, a rat or the like is immunized using commercially available HMGB1, and the antibody-producing cell or spleen cell is fused with a myeloma cell to obtain a hybridoma. The hybridoma is cloned, and a clone producing an antibody which specifically reacts with HMGB1 is screened. The clone is cultured, and a secreted monoclonal antibody may be purified.

The kind of the anti-HMGB1 monoclonal antibody used in the present invention is not specifically limited. For example, a human-type antibody and a complete human antibody may be used.

A dosage form of the cerebral vasospasm inhibitor of the present invention is not specified. However, liquid preparations such as solutions and emulsion preparations are preferable for the administration as injection, taking into consideration the fact that an anti-HMGB1 monoclonal antibody as an active ingredient is a peptide.

A solution isotonic to plasma, such as pH-adjusted physiological saline and aqueous solution of glucose, can be used as a solvent for a liquid preparation. When an antibody is freeze-dried together with a salt or the like, pure water, distilled water, sterilized water and the like can also be used. The concentration may be that of a common antibody preparation; and may be about 0.1 to 1 mg/mL generally, and about 0.02 to 0.2 mg/mL for drip infusion. However, the osmotic pressure of an injection needs to be similar to that of plasma.

In the present invention, "inhibition" implies both concepts of the inhibition of occurrence of cerebral vasospasm, i.e. "prevention", and the relief of occurred cerebral vasospasm, i.e. "treatment". Accordingly, the cerebral vasospasm inhibitor of the present invention may be administered for the preventive purpose between subarachnoid hemorrhage and the occurrence of cerebral vasospasm, or for the treatment purpose after the occurrence of cerebral vasospasm.

Cerebral vasospasm is observed in half or more of the patients in 3 to 14 days after subarachnoid hemorrhage. The mechanism of development of subarachnoid hemorrhage to cerebral vasospasm is not yet completely clarified, though some factors have been suggested and multiple factors are supposed to be involved in a complicated manner. Therefore, the blood level of the cerebral vasospasm inhibitor of the present invention should be maintained in the cerebral blood vessel after subarachnoid hemorrhage or after the occurrence of cerebral vasospasm. Accordingly, the cerebral vasospasm inhibitor of the present invention is preferably administered in a plurality of times or continuously after subarachnoid hemorrhage.

The frequency and the dose for administration in a plurality of times may be appropriately adjusted according to whether the administration is before or after the occurrence of cerebral vasospasm, or the patient's condition, or the like. As shown in the Examples described later, a remarkable effect in inhibition of cerebral vasospasm was obtained after administration of an anti-HMGB1 monoclonal antibody two times at the dose of 2 mg per one time in subarachnoid hemorrhage model rabbits weighing about 3 kg. Based on the result, the dose of an anti-HMGB1 monoclonal antibody for humans may be 0.1 to 2 mg/kg, more preferably 0.2 to 2 mg/kg per one time, and administration two times per day is acceptable. The administration method is not limited, and for example administration may be carried out by intravenous injection, and in emergency, administration via cisternal drainage placed in a subarachnoid hemorrhage surgery is acceptable.

The concentration in a preparation and the dose for continuous administration may be appropriately adjusted. For example, a liquid preparation of 0.02 to 0.2 mg/mL can be administered by drip infusion over 2 to 4 hours two times a day.

When a patient of cerebral vasospasm survives for about 14 days after subarachnoid hemorrhage, the cerebral vasospasm generally undergoes spontaneous regression. Accordingly, after about 14 days from subarachnoid hemorrhage, the dose of the cerebral vasospasm inhibitor of the present invention can be gradually reduced in consideration of the patient's condition or the like.

The cerebral vasospasm inhibitor of the present invention can effectively inhibit cerebral vasospasm which occurs after subarachnoid hemorrhage and may have serious adverse effects on the patient. As compared with the antibody agents currently used, the inhibitor is very unlikely to cause serious side-effects. Therefore, the cerebral vasospasm inhibitor of the present invention is very useful as a medicament that inhibits cerebral vasospasm for which no effective method has been available, prevents sequelae and promotes the patient's comeback to normal life.

EXAMPLES

Hereinafter, the present invention is explained in more detail with reference to the Examples. The present invention should not be naturally limited by the following Examples, and can be implemented after appropriate modification within the range compatible with the spirit of the description above and below. Such a modification is embraced by the technical scope of the present invention.

Example 1

Preparation of an Anti-HMGB1 Monoclonal Antibody (a) Immunization of a Rat

A commercially available 1 mg/mL mixture of bovine thymus-derived HMGB1 and HMGB2 (manufactured by Wako Pure Chemical Industries Ltd., code No. 080-070741) was taken into a 2 mL glass syringe; and was gradually mixed with an equal volume of a Freund's complete adjuvant taken into another 2 mL glass syringe via a connecting tube, to give an emulsion. Into the footpads of the hind limbs of a sevoflurane-anesthetized rat, 0.1 mL each, 0.2 mL in total, of the emulsion was injected. Blood was sampled from the cervical vein two weeks later, and the increase of the antibody titer was confirmed. Then, the swollen iliac lymph nodes were aseptically isolated 5 weeks after the injection. About $6 \times 10^7$ cells could be recovered from the two lymph nodes thus obtained.

(b) Cell Fusion and Cloning

The iliac lymph node cells and mouse myeloma SP2/O-Ag14(SP2) cells were fused using polyethylene glycol. The resultant fused cells were distributed onto a 96-well microplate. The first ELISA screening was carried out one week later, and the cells in the positive wells were subjected to the secondary screening by Western blot analysis. The positive cells were transferred to a 24-well microplate, cultured until the cells became almost confluent (about $2 \times 10^5$), and frozen for preservation in liquid nitrogen using 0.5 mL of a frozen culture medium which was a GIT medium added with 10% of bovine fetal serum and 10% of dimethylsulfoxide. These frozen cells were thawed and were cloned in a 96-well microplate.

(c) Purification of Antibody

The positive cells were cultured in large scale for 2 weeks in a rotating culture apparatus manufactured by Vivascience Co., to give an antibody fluid of a concentration of 2 to 3 mg/mL. The antibody fluid was mixed with an affinity gel: MEP-HyperCel manufactured by Invitrogen Co., at a neutral pH, so that the anti-HMGB1 antibody might be specifically bound to the gel. The antibody specifically bound to the gel was eluted with a glycine-hydrochloric acid buffer (pH 4). The eluate was concentrated in an ultrafiltration device, followed by further purification through a SEPHAROSE (cross-linked agarose beads) CL6B gel filtration column (2 cm in diameter×97 cm in length).

The obtained monoclonal antibody is an antibody specifically recognizing the C-terminal sequence of the HMGB1 protein, 208EEEDDDDE215 (SEQ ID NO: 1) (E stands for glutamic acid and D stands for aspartic acid) as an epitope. Though HMGB2 is similar to HMGB1, the monoclonal antibody of the present invention does not bind to HMGB2, since HMGB2 lacks the sequence: DDDDE (SEQ ID NO: 2) after 211; however, the antibody can specifically recognize and bind to only HMGB1.

Example 2

One week before twelve male rabbits weighing each about 3 to 3.5 kg, obtained from Charles River Laboratories Japan Inc., were made into subarachnoid hemorrhage models, the animals were anesthetized with ketamine hydrochloride (50 mg/kg, intramuscular administration) and pentobarbital (20 mg/kg, intravenous administration). Then, a contrast medium was infused via a catheter inserted from the right femoral artery to the origin of the left vertebral artery, and the basilar artery was photographed by angiography. On the day of the preparation of a subarachnoid hemorrhage model, each rabbit was anesthetized with ketamine hydrochloride (50 mg/kg, intramuscular administration) and pentobarbital (20 mg/kg, intravenous administration), and 1 mL of arterial blood was taken. The arterial blood thus taken was injected into the cisterna magna, i.e. the cerebellomedullary cistern, of the same animal. Then, the animal was held with the head downward for 30 minutes to obtain a subarachnoid hemorrhage model.

Separately, 2 mg of the rat anti-bovine HMGB1 monoclonal antibody purified in Example 1 was dissolved in 1 mL of a phosphate buffer, to obtain an antibody solution. Into four subarachnoid hemorrhage model rabbits, 1 mL of the antibody solution, i.e. 2 mg of the anti-bovine HMGB1 monoclonal antibody, was intravenously injected at 1 and 24 hours after the experimental subarachnoid hemorrhage.

Figure 2:
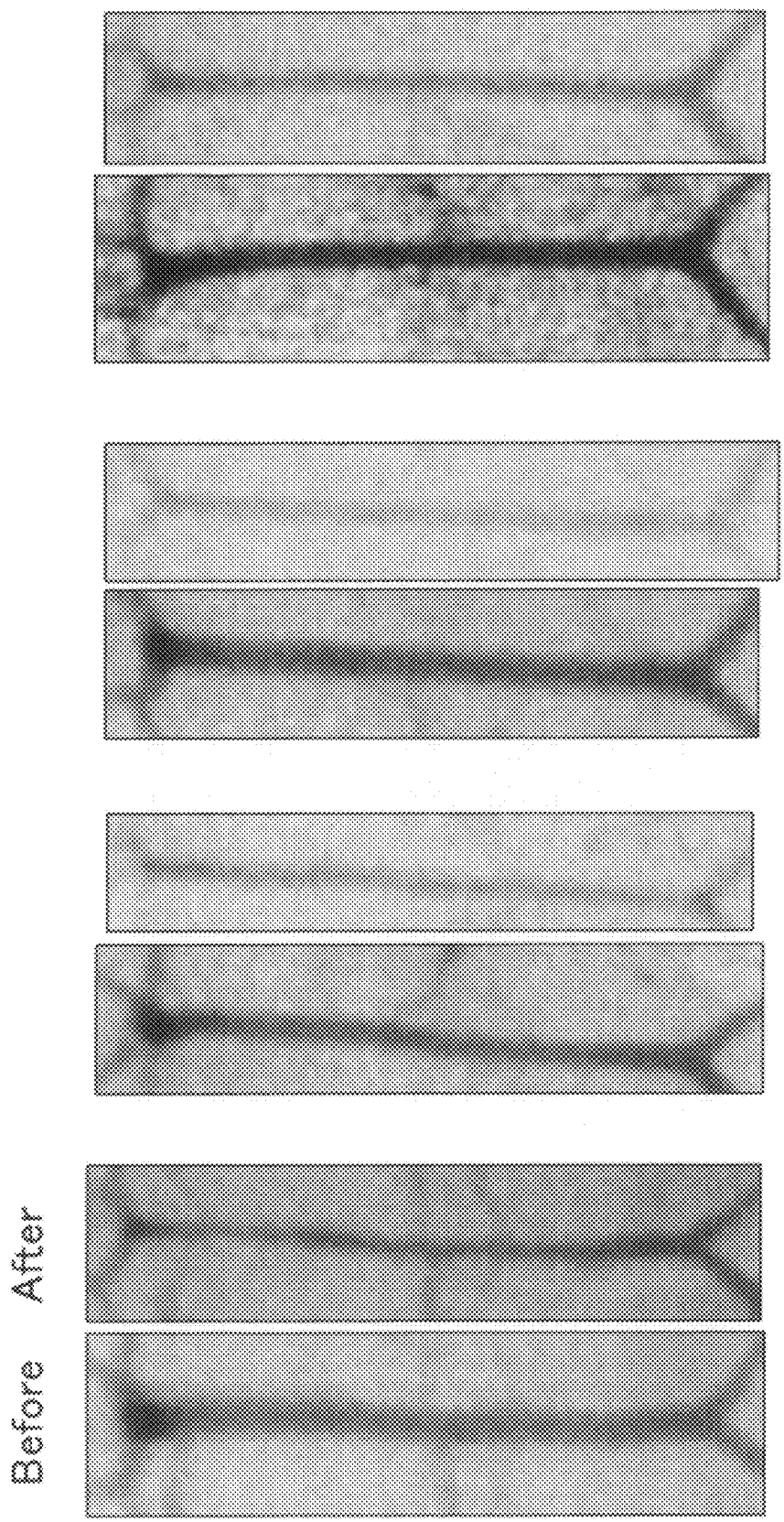
FIG. 2 is contrast images of a basilar artery before and after subarachnoid hemorrhage in an IgG-administered animal group of subarachnoid hemorrhage model rabbits. In each pair of the photographs in the figure, a photograph before subarachnoid hemorrhage, represented as "before", is on the left; and a photograph after subarachnoid hemorrhage, represented as "after", is on the right. In each pair, the vascular diameter obviously becomes smaller, in other words, severe cerebral vasospasm is observed, after subarachnoid hemorrhage (in the right photographs).
Figure 3:
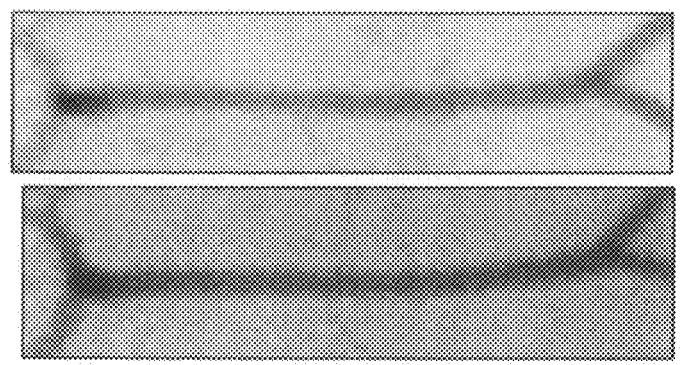
FIG. 3 is contrast images of a basilar artery before and after subarachnoid hemorrhage in an animal group of subarachnoid hemorrhage model rabbits administered with the antibody of the present invention. In each pair of the photographs in the figure, a photograph before subarachnoid hemorrhage, represented as "before", is on the left; and a photograph after subarachnoid hemorrhage, represented as "after", is on the right. In each pair, cerebral vasospasm in the photograph after subarachnoid hemorrhage (in the right photographs) is obviously inhibited as compared with the untreated animal group in FIG. 1 and the IgG-administered animal group in FIG. 2.
Figure 3:
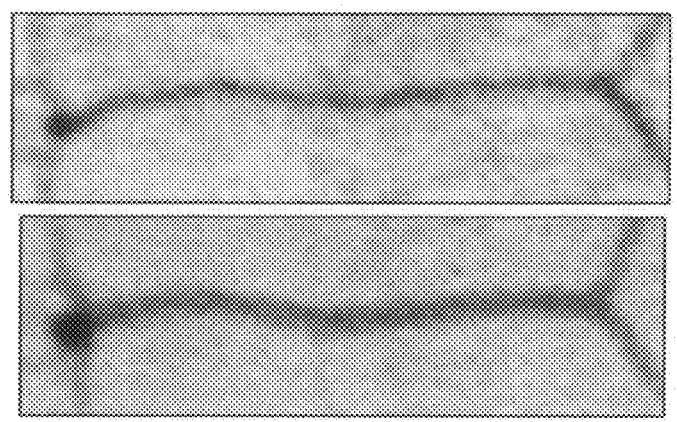
Figure 3:
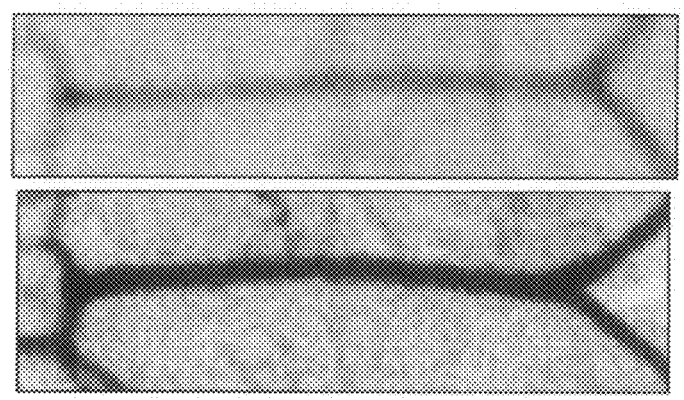
Figure 3:
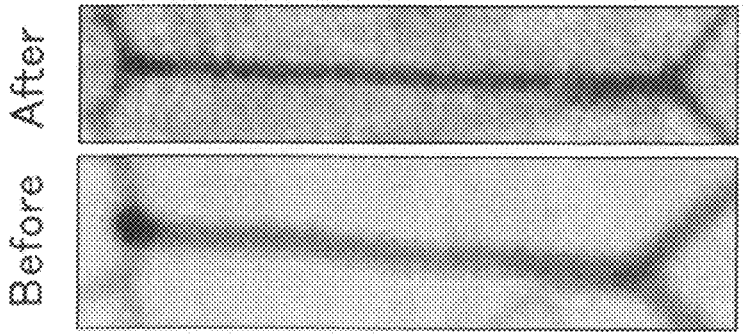
Figure 4:
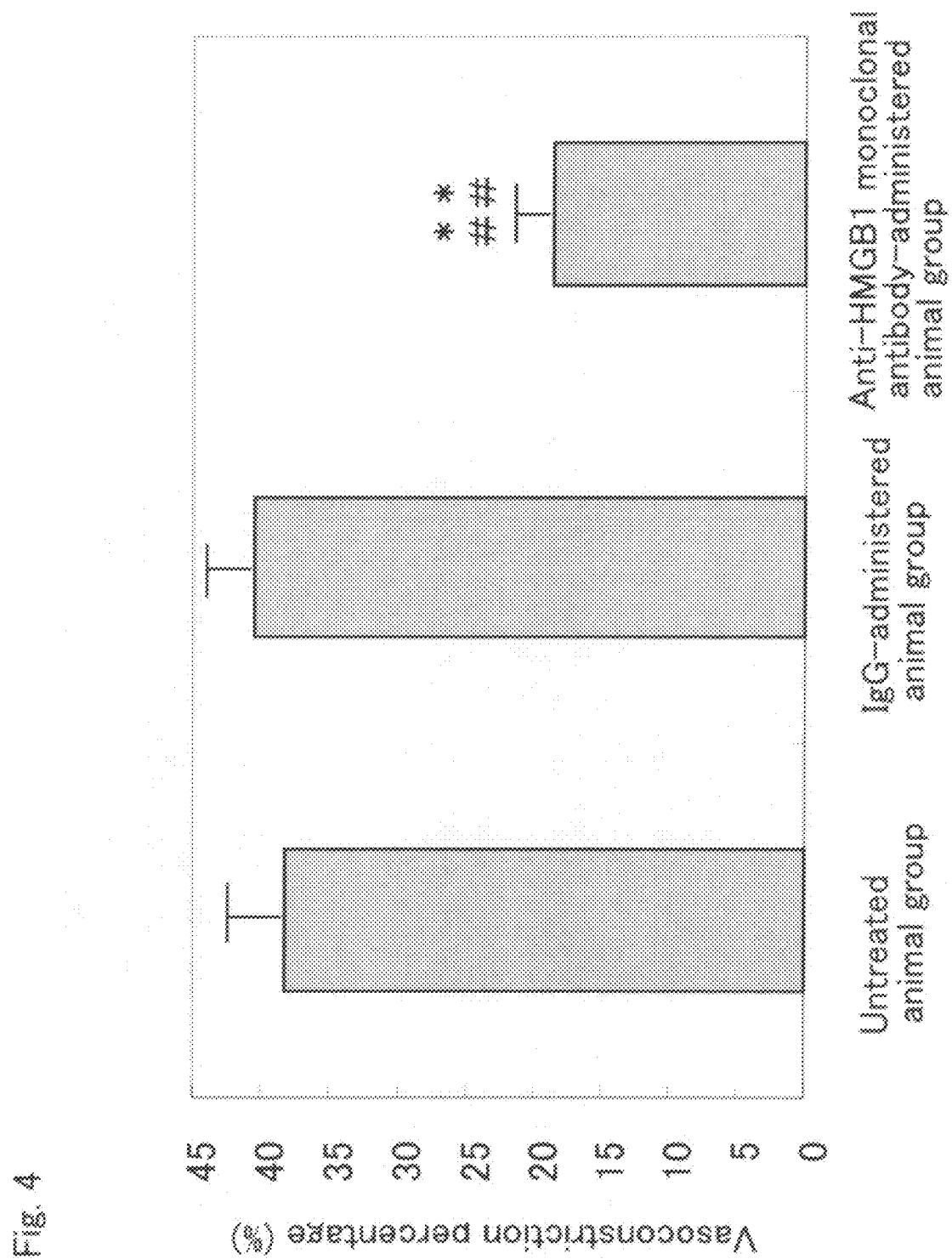
FIG. 4 is a graph for comparison of the vasoconstriction percentage among the untreated animal group, the IgG-administered animal group and the group of animals administered with the anti-HMGB1 monoclonal antibody of the present invention. The effect of inhibiting cerebral vasospasm by the anti-HMGB1 monoclonal antibody of the present invention is significantly superior to that in the case of no treatment and that in the case of IgG administration.

The basilar artery was photographed by angiography in the same way as described above three days after the experimental subarachnoid hemorrhage. For comparison, angiography was carried out for 4 rabbits that received no administration of the anti-bovine HMGB1 monoclonal antibody, which is represented as "an untreated animal group", and 4 rabbits that received administration of rat normal polyclonal immune globulin G (2 mg) having many antibody activities, which is represented as "an IgG-administered animal group". The four photographs per group, i.e. a total of twelve photographs, are shown in FIGS. 1 to 3. FIG. 1 is an example of the untreated animal group, FIG. 2 is an example of administering polyclonal immune globulin G, and FIG. 3 is an example of administering the anti-HMGB1 monoclonal antibody of the present invention. In addition, the inner diameter was measured at nine sites of the basilar artery from the photographs using the NIH Image J (National Institute of Health) for determination of the shrinkage ratio of the inner diameter after subarachnoid hemorrhage, and the mean value of the measurements was calculated for each individual. From the mean values of the individual animals, the mean shrinkage ratio in each group was calculated. A t-test was carried out for any significant difference among groups. The results are shown in Table 1 and FIG. 4. In FIG. 4, "**" represents a significant difference at $p<0.01$ as compared with the untreated animal group and "##" represents a significant difference at $p<0.01$ as compared with the IgG-administered animal group.

TABLE 1

|  | Vasoconstriction percentage (%) | Mean value (%) |
|---|---|---|
| Untreated animal group | 47.46 | 38.01 |
|  | 30.23 |  |
|  | 27.95 |  |
|  | 46.64 |  |
| IgG-administered animal group | 47.22 | 40.53 |
|  | 40.33 |  |
|  | 43.45 |  |
|  | 31.11 |  |
| Anti-HMGB1 monoclonal antibody | 10.83 | 18.57 |
|  | 13.04 |  |
|  | 23.96 |  |
|  | 26.43 |  |

As shown in FIG. 1, the basilar artery of the rabbit without administration of an antibody became narrower after experimental subarachnoid hemorrhage and had severe cerebral vasospasm. As shown in FIG. 2, the rabbit given IgG also had severe cerebral vasospasm. In contrast, as shown in FIG. 3, the width of the basilar artery of the rabbit given the anti-HMGB1 monoclonal antibody of the present invention was maintained to a considerable degree and cerebral vasospasm was remarkably inhibited. The inhibition effect of cerebral vasospasm by the anti-HMGB1 monoclonal antibody of the invention was statistically significantly superior to that in the case of no treatment and that in the case of administration of IgG. Therefore, it was demonstrated that the cerebral vasospasm inhibitor of the present invention is capable of remarkably inhibiting cerebral vasospasm.

The invention claimed is:

1. A method of preventing cerebral vasospasm occurring after subarachnoid hemorrhage, comprising administering an anti-HMGB1 monoclonal antibody, wherein the anti-HMGB1 monoclonal antibody recognizes 208EEED-DDDE215 (SEQ ID NO: 1) as an HMGB1 epitope, to a patient thereby preventing cerebral vasospasm occurring after subarachnoid hemorrhage.

2. The method according to claim 1, wherein 0.2 to 2 mg/kg of the anti-HMGB1 monoclonal antibody is administered each time.

3. The method of claim 1, wherein the anti-HMGB1 monoclonal antibody is administered continuously after subarachnoid hemorrhage.

4. The method of claim 1, wherein the anti-HMGB1 monoclonal antibody is administered by intravenous injection.

5. The method of claim 1, wherein the anti-HMGB1 monoclonal antibody is administered a plurality of times after subarachnoid hemorrhage.

* * * * *